United States Patent [19]

Nath et al.

[11] Patent Number: 5,367,070
[45] Date of Patent: Nov. 22, 1994

[54] METHOD FOR MAKING FERROMAGNETIC PORPHIN COMPOUNDS

[75] Inventors: Amar Nath, Bala Cynwyd; Nikolai Kopeley, Philadelphia, both of Pa.; Som D. Tyagi, Wilmington, Del.

[73] Assignee: Drexel University, Philadelphia, Pa.

[21] Appl. No.: 13,885

[22] Filed: Feb. 5, 1993

[51] Int. Cl.$^5$ .......................................... C07D 487/22
[52] U.S. Cl. .................................... 540/145; 540/140
[58] Field of Search ................................ 540/140, 145

[56] References Cited

U.S. PATENT DOCUMENTS 4,892,941  1/1990  Dolphin et al. .................... 540/145
5,099,014  3/1992  Young ................................ 540/145

OTHER PUBLICATIONS

Shashoua, Jour. Amer. Chem. Soc., vol. 87, No. 18 1965 pp. 4044–4048.
Lelievre et al., Jour. Amer Chem Soc., vol. 114, No. 12 1992, pp. 4475–4479.
Chem Abstract: Hisashi et al., vol. 116:226732r.
Chem Abstract: Hisashi et al ., vol. 117:130770w.
A. Harutyunyan et al., "Organic Ferromagnets on Base of Metal-Phythalocyanines Doped by Alcali Metals", XIV(4) *Materials Science* 121–126 (1988).
E. Kirschner, "ACS Meeting Highlights Advance In Organic Magnets", *Chemical Week* (Apr. 15, 1992).
C. Landee et al., "Molecular Magnetic Materials-Applications Discussion", *Molecular Magnetic Materials* 395–398 (1991).
J. Manriquez et al., "A Room-Temperature Molecular-/Organic-Based Magnet", 252 Science pp. 1415–1416 (Jun. 7, 1991).
Z. Min-Guang, "An Ambient Temperature-Stable Organometallic Ferromagnet", 3 *J. Phys. Condens. Matter* 6695–6702 (1991).

*Primary Examiner*—Mukund J. Shah
*Assistant Examiner*—Pavanaram K. Sripada
*Attorney, Agent, or Firm*—Panitch Schwarze Jacobs & Nadel

[57] ABSTRACT

Ferromagnetic porphin compounds may be produced by heating a non-ferromagnetic porphin compound having a central transition metal atom in the non-ferromagnetic porphin molecule and at least some of the pyrrole rings of the non-ferromagnetic porphin molecule having benzene or phenyl groups substituted on or integral with said rings. The non-ferromagnetic porphin compound is heated in the substantial absence of oxygen to a temperature sufficient to pyrolyze at least a portion of the benzene or phenyl groups of the non-ferromagnetic porphin compound. A ferromagnetic porphin compound is formed, which is inherently magnetic and is capable of retaining magnetism when exposed to a magnetic field. The resulting ferromagnetic porphin compounds retain their ferromagnetic properties even up to about 473° K. in air and to much higher temperatures in vacuum or an inert atmosphere.

14 Claims, 2 Drawing Sheets

1

METHOD FOR MAKING FERROMAGNETIC PORPHIN COMPOUNDS

FIELD OF THE INVENTION

The present invention relates to a method for making insulating organic ferromagnetic materials and, more particularly, to making ferromagnetic porphin compounds which provide substitutes for insulating magnetic materials, such as ferrite compounds.

BACKGROUND OF THE INVENTION

As new or improved magnetic applications or devices are developed, there is an increasing need for insulating magnetic materials which are chemically stable up to critical or Curie temperatures ($T_c$) in excess of 125° C. Such magnetic materials may be substituted for ferrites and other insulating magnetic compounds in applications such as radio frequency transformers, bulk magnets, magnetic and magneto-optic recording materials, for example. Such magnetic materials may also be included in photomagnetic switches, integrated optical devices, colloidal dispersions ("ferrofluids" and magnetic inks), thin film and multilayer magnets, magnetostrictive sensors, microwave materials, magnetic bubbles and soft magnetic materials with low coercive fields for AC motors, generators and transformers, as well as for magnetic imaging and transducers for medical implants, if the magnetic material is biocompatible.

Several low temperature organic and inorganic ferromagnetic compounds have been disclosed in the prior art. The reported organic ferro- and ferri- magnets are generally poorly characterized and yields are limited and not reproducible. J. Manriquez et al. "A Room-Temperature Molecular/Organic-Based Magnet", 252 Science 1415 (1991) discloses a molecular organic ferromagnetic compound having an empirical composition of $V(TCNE_x) \cdot y(CH_2Cl_2)$, where TCNE is tetracyanoethylene, x is about 2 and y is about ½. The compound undergoes thermal decomposition at 350° K. (77° C.).

Z. Min-Guang, "An Ambient Temperature-Stable Organometallic Ferromagnet", 3 J. Phys. Condens. Matter 6695-6702 (1991) discloses an organometallic ferromagnet having a nominal composition of $Cd_2Fe_2C_{36}H_{38}N_4O_4$. A magnetic hysteresis loop for the compound was observed with finite residual magnetization and coercivity at room temperature. However, the Mössbauer probe $^{57}Fe$ in the compound does not sense any magnetic field and so the authors attributed the observed ferromagnetism to the organic free radicals.

A. Harutyunyan et al., "Organic Ferromagnets on Base of Metal-Phthalocyanines Doped by Alcali Metals," XIV(4) Materials Science 121-26 (1988) discloses a ferromagnetic compound formed by doping metal-phthalocyanines with alkali metals. The Curie temperature ($T_c$) for [2Na-FePc] was found to be 590° K. from the plot of saturation magnetization versus temperature. The ($T_c$) for the cobalt compound was much higher and was not determined. However, the disclosed compounds are only stable in air up to 350° K. (77° C.).

There is also disclosed in the art an unstable manganese tetraphenylporphyrin (TPP)/tetracyanoethylene (TCNE) salt polymer which burst into flames on contact with air.

None of the prior art magnetic materials discussed above is stable at temperatures on the order of about 473° K. (200° C.) in an atmospheric environment and to much higher temperatures in vacuum or an inert atmosphere. There is a long-felt and unfulfilled need in the art for an insulating organic ferromagnetic material capable of remaining stable at temperatures in excess of 125° C.

BRIEF SUMMARY OF THE INVENTION

Briefly stated, the present method is for making a ferromagnetic porphin compound from a non-ferromagnetic porphin compound having a central transition metal atom in the non-ferromagnetic porphin molecule. At least some of the pyrrole rings of the non-ferromagnetic porphin molecule have benzene or phenyl groups substituted on or integral with the pyrrole rings. According to the present method, the non-ferromagnetic porphin compound is heated in the substantial absence of oxygen to a temperature sufficient to pyrolyze at least a portion of the benzene or phenyl groups of the non-ferromagnetic porphin compound. A ferromagnetic porphin compound is formed which is inherently magnetic and retains magnetism upon exposure to a magnetic field. Optionally, the non-ferromagnetic porphin compound may be pretreated to induce self-catalysis.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred, it being understood, however, that the invention is not limited to the specific methods and instrumentalities disclosed. In the drawings.

DETAILED DESCRIPTION OF THE PREFERRED EMBODIMENTS

Figure 1A:
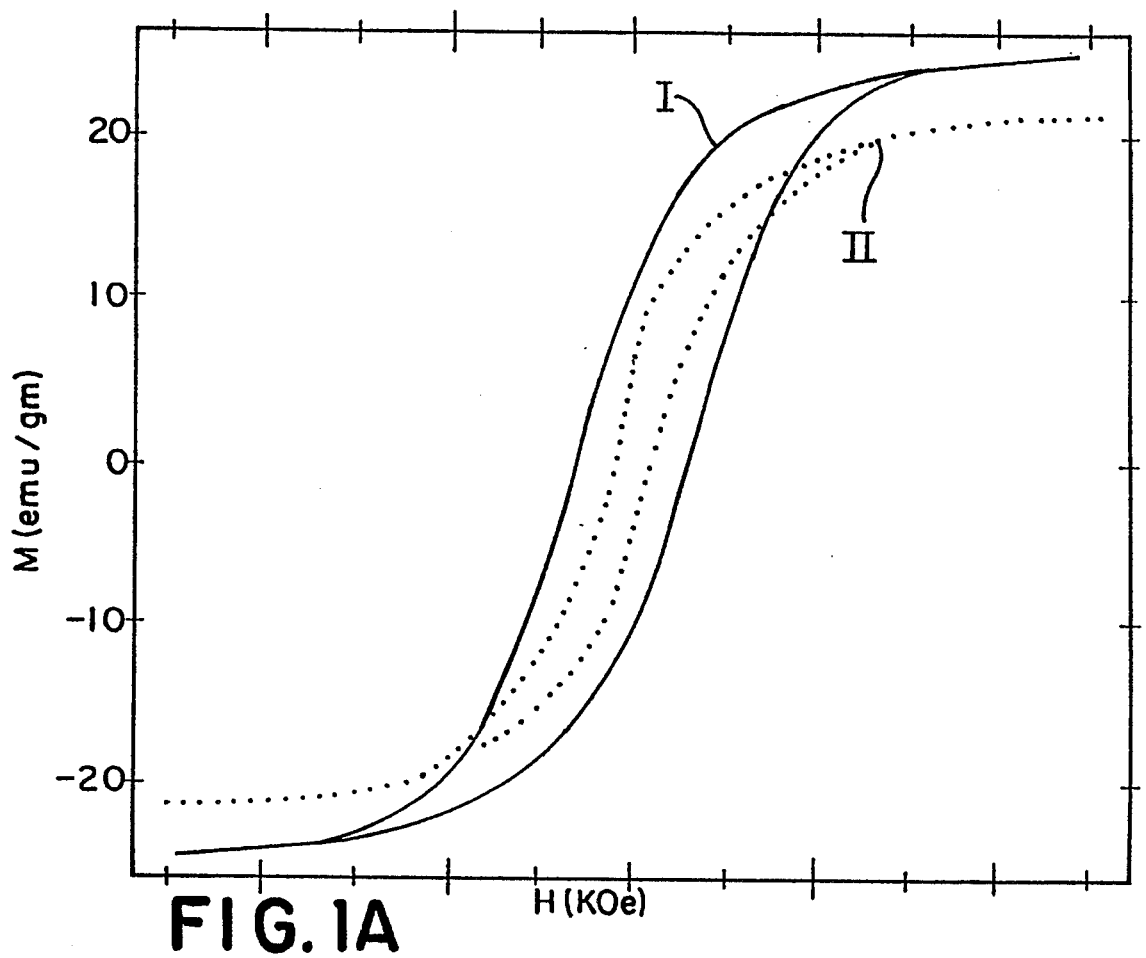
FIGS. 1A and 1B are two graphs of magnetization (M) as a function of magnetic field (H) of several ferromagnetic porphin compounds produced by the method of the present invention.

By the present method, ferromagnetic organometallic materials which are stable in air at temperatures in excess of 125° C. (398° K.), and generally up to about 200° C. (473° K.) may be prepared. The ferromagnetic porphin compounds produced according to the present method are prepared from non-ferromagnetic porphin compounds, preferably of the β-crystalline type. The non-ferromagnetic porphin compound has a central transition metal atom in the molecule. At least some of the pyrrole rings of the molecule have benzene or phenyl groups substituted on or integral with the pyrrole rings. Examples of suitable non-ferromagnetic porphin compounds include phthalocyanine and tetraphenyl-porphinate. The non-ferromagnetic porphin compound includes a transition metal, preferably selected from cobalt, manganese, iron and nickel.

The non-ferromagnetic porphin compound may optionally be pretreated to catalyze the formation of the ferromagnetic porphin compound. Preferably, both the pretreatment and heating of the non-ferromagnetic porphin compound are carried out in the substantial absence of atmospheric oxygen. It is believed that excess oxygen may be adsorbed by the non-ferromagnetic porphin compound and adversely effect formation of the ferromagnetic porphin compound. For example, phthalocyanines are notorious for adsorbing oxygen from the atmosphere. Therefore, as presently preferred, both the pretreatment and heating steps of the present method are carried out in the presence of an inert gas, such as argon or nitrogen.

Alternatively, the non-ferromagnetic porphin compound may be pretreated by gamma irradiation or by heating the compound to a pretreatment temperature lower than the heating temperature, such as about 100° C. for about 20 hours. By pretreating the non-ferromagnetic porphin compound, the subsequent heating temperature and/or time may be reduced.

To form the ferromagnetic porphin compound, the non-ferromagnetic porphin compound is heated in the substantial absence of oxygen to a temperature sufficient to pyrolyze at least a portion of the benzene or phenyl groups of the non-ferromagnetic porphin compound. A ferromagnetic porphin compound is formed which is inherently magnetic and is also capable of retaining magnetism upon exposure to a magnetic field. It is believed that at least a portion of the non-ferromagnetic porphin compound is pyrolyzed since a corresponding loss of mass is observed. It is also believed that this pyrolytic effect may be reduced by pretreatment of the non-ferromagnetic porphin compound to induce self-catalysis, as discussed above.

Mössbauer studies of iron phthalocyanine and cobalt ($^{57}$Co) phthalocyanine indicate that the transition metal-$N_4$ moiety and the aromatic character of the porphin ring are retained after heating according to the present method and that there is a fairly strong interaction between the central transition metal atom and axially situated aromatic rings or nitrogens of neighboring molecules. The axial interactions are believed to provide a pathway for ferromagnetism.

As presently preferred, the non-ferromagnetic porphin compound is heated at a temperature of about 450° C. to about 700° C., and, more preferably, about 600° C. to about 700° C. for several hours to form the ferromagnetic porphin compound. When the non-ferromagnetic porphin compound is pretreated to induce catalysis, it is believed that the subsequent heating temperature may be reduced, preferably to about 475° C. or less.

The magnetic properties of the resulting porphin-derived compound were examined using the standard vibrating sample magnetometer technique. The magnetization vs. magnetic field plots (FIGS. 1A and 1B) exhibit the ferromagnetic characteristics of remanence, coercivity, and technical saturation in externally applied magnetic fields of 0.5 to 0.6 Tesla.

The present method will now be illustrated in more detail by reference to the following specific, non-limiting example.

EXAMPLE

Each of the analytical grade chemicals used in this Example were obtained from Aldrich Chemical Co. of Milwaukee, Wis. and used without further purification unless otherwise specified below. Manganese, iron, cobalt and nickel phthalocyanine compounds, respectively, were prepared by converting each α-crystalline compound to the β-crystalline form by conventional refluxing in carbon tetrachloride or toluene for several hours.

Each of the phthalocyanine compounds and cobalt tetraphenylporphinate were heated in an argon flow at slightly positive pressure to prevent atmospheric oxygen from contacting the non-ferromagnetic porphin compounds. Each sample was heated at a temperature of 600° C. or 700° C. for a period of time, as specified in Table I.

TABLE I

| Non-ferromagnetic Porphin Compound | Temperature (°C.) | Time (hrs) | Saturation Magnetization $M_s$ (emu/gm) | Remanent Magnetization (emu/gm) | Coercivity $H_c$ (Oe) |
|---|---|---|---|---|---|
| Manganese phthalocyanine | 700 | 15 | 4.3 | 0.75 | 150 |
| Nickel phthalocyanine | 700 | 4 | 9.3 | 2.2 | 110 |
| Iron phthalocyanine | 600 | 15 | 21 | 7.8 | 200 |
| Cobalt phthalocyanine | 600 | 12 | 24.2 | 10 | 650 |
| Cobalt tetraphenylporphinate | 600 | 5 | 12.9 | 7.0 | 800 |

The chemical composition of each ferromagnetic porphin compound formed by the present method (hereinafter referred to as the "product") was determined using standard elemental analyses and spectrophotometric estimation of cobalt. Several of the ferromagnetic products were analyzed by X-ray powder diffraction (using a Siemens D-500 diffractometer, CuK$_\alpha$ and CrK$_\alpha$ radiation, graphite monochrometer, scanning range: 2°-90°2θ, scanning rate: 1°2θ/min), IR spectroscopy (Perkin Elmer FTIR-1600 spectrophotometer, pellets with KBr, spectral range: 400–4000 cm$^{-1}$, resolution: 2 cm$^{-1}$) and thermogravimetric analysis (TGA) (Dupont Thermogravimetric Analyzer M951) in air, with a heating rate of 10° C./min. Both absorption and emission variants Mossbauer spectroscopy were used to characterize the cobalt and iron-based products. Absorption spectra of the product prepared from iron phthalocyanine were recorded conventionally, as described in V. Goldanskii et al. (Ed.), *Chemical Application of Mossbauer Spectroscopy* (Academic Press 1968). Emission Mossbauer effect measurements were conducted using a synthesized sample of cobalt ($^{57}$Co) phthalocyanine as the source of γ-radiation and K$_4$[F(CN)$_6$]·3H$_2$O (0.25 mg $^{57}$Fe/cm$^2$) as the moving absorber. The Mossbauer velocity scale was inverted to correspond to the absorption measurements. All values of isomer shift were given relative to α-Fe. Magnetization (M) versus magnetic field (H) graphs, such as those set forth in FIG. 1, were obtained using a standard vibrating sample magnetometer (VSM).

After heating according to the present method, each of the products was in the form of a grayish-black ferromagnetic powder. When the sample of cobalt phthalocyanine was heated at 600° C. for twelve hours under an argon flow, the resulting product had 25% less mass than the starting cobalt phthalocyanine compound. More specifically, the cobalt content of the starting cobalt phthalocyanine compound was 10.3%. After heating, the cobalt content of the product was about 12.6 mass percent. The mass lost during thermal treatment of the iron phthalocyanine was much higher, above about 30%. The cobalt-to-nitrogen ratio of the cobalt phthalocyanine compound was 1:8, whereas the ratio of the product was approximately 1:4. Therefore, it is believed that at least a portion of the outer rings of the cobalt phthalocyanine compound was pyrolyzed.

Infrared spectroscopy analysis of the product formed from the cobalt phthalocyanine compound indicated a lack of crystallinity. An X-ray diffractogram of the product did not show any reflections, which may indicate that the ferromagnetic material has an amorphous nature, or the presence of an amorphous shell around crystallites. However, Mössbauer studies of the product showed the absence of superparamagnetism. This rules out the possibility of the product having microcrystalline particles having an average diameter less than 200 angstroms.

Figure 1B:
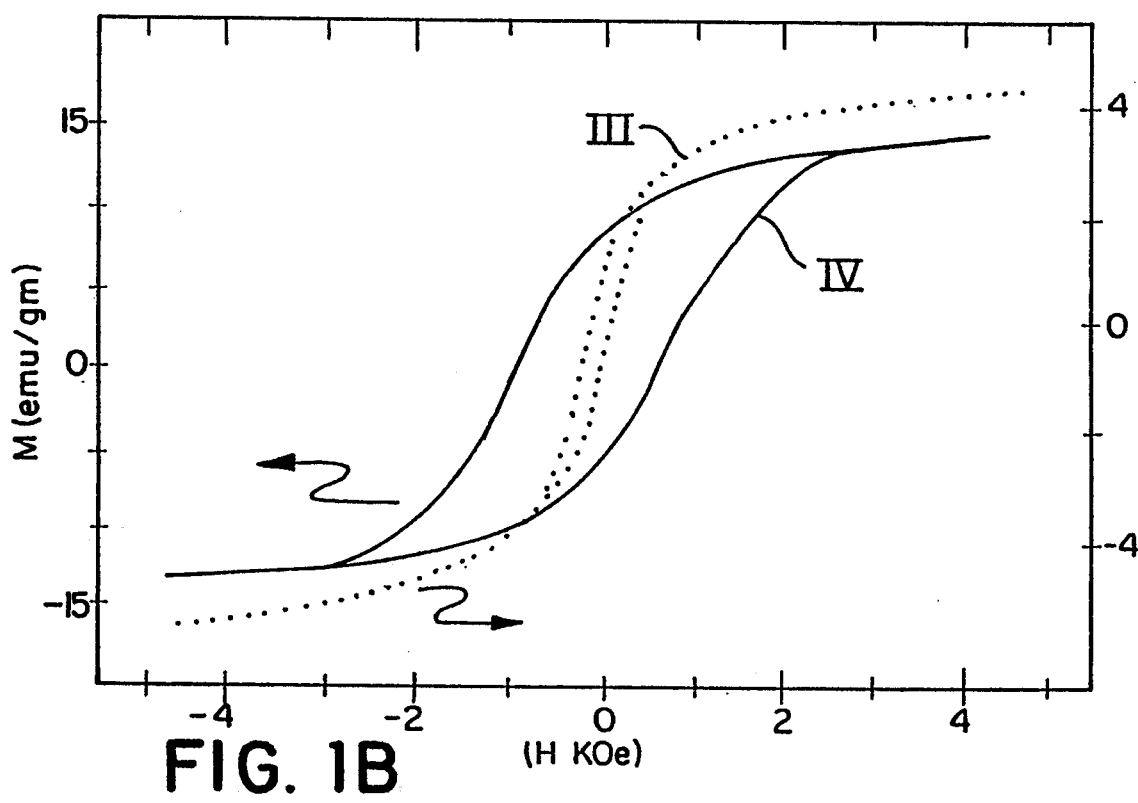

Graphs of magnetization (M in emu/gm) as a function of magnetic field (H in kOe) showing hysteresis loops for the products formed from cobalt phthalocyanine, iron phthalocyanine, manganese phthalocyanine and cobalt tetraphenylporphinate (Curves I-IV, respectively) products prepared according to the present method are shown in FIGS. 1A and 1B. The saturation magnetization for each product was measured at a coercivity of 5 kOe. The saturation field exceeds the field attainable with the magnet. A summary of the magnetic parameters determined from FIG. 1 is set forth in Table I. The shape of the loop of each of the products may vary based upon processing conditions, such as heating temperatures, time, etc. Magnetic phases were also detected in the thermally treated copper phthalocyanine product, although the yield was small.

Figure 2:
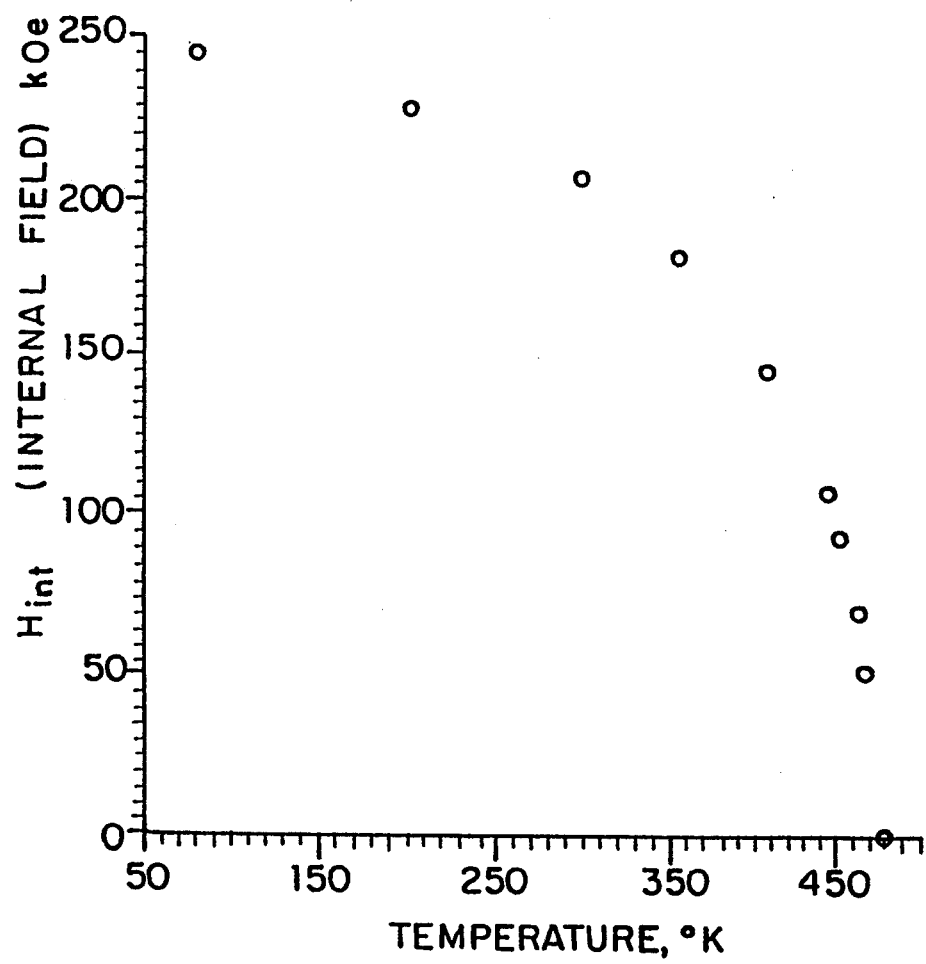
FIG. 2 is a graph of internal magnetic field ($H_{int}$) as a function of temperature (° K.) for an iron ferromagnetic porphin compound produced according to the method of the present invention.

A Mössbauer probe $^{57}$Fe was used to sense the internal magnetic field for the iron and cobalt phthalocyanine products as a function of temperature. The hyperfine interaction arises from polarization of the s-electrons by the magnetism of the unpaired d-electrons. The Curie temperature ($T_c$) for the product of the thermally treated iron phthalocyanine compound was determined by plotting the hyperfine field (kOe) as a function of temperature (° K.), as shown in FIG. 2. The extent of the six-line spectra determines the hyperfine field and the sextet collapses into a doublet above the Curie temperature of about 475° K. Mössbauer spectroscopy is commonly used for determining the Curie temperature. The measurements were made in a vacuum oven to avoid interaction of the product with atmospheric oxygen. The quadrupole splitting and isomer shift of the doublet at 478° K. were observed to be 0.44 and 0.016 mm/sec (0.16 mm/sec at room temperature), respectively. The relative abundance of the doublet increases from 16% at 443° K. to 50% at 468° K. Both the sextet and the doublet exist simultaneously in this temperature range. This indicates that there is a distribution in Curie temperature without a corresponding variation in internal magnetic field.

The Mössbauer spectra for the product produced by heating the cobalt phthalocyanine compound, when exposed to an external magnetic field of about 0.43 Tesla, shows an increase in the internal magnetic field of the product, as expected for a ferromagnetic material. Analysis of the Mössbauer spectrum indicates about 50% alignment of the magnet moments. The internal magnetic field of the product varies from 331.5 kOe at 80° K. to about 277 kOe at 890° K. The Curie temperature lies well above 890° K. Again, the measurements were carried out in a vacuum oven. When the product was heated in air at 200° C. for 24 hours, about 66% of the original compound survived. Thermogravimetric analysis of the product in air showed decomposition only at about 300° C. with accompanying occurrence of combustion.

It should be emphasized that there were no indications of the formation of metallic clusters in the products. For example, the internal magnetic fields observed for the iron and cobalt phthalocyanine products at room temperature were 206.2 and 323.4 kOe, respectively. The corresponding internal magnetic fields for elemental iron and cobalt were 330 and 310 kOe, respectively, as sensed by $^{57}$Fe.

Elemental manganese is antiferromagnetic. Yet, as shown in curve II of FIG. 1, the product resulting from thermal treatment of manganese phthalocyanine, according to the method of the present invention, exhibits ferromagnetic properties, which clearly shows that the ferromagnetism observed is not due to the trivial possibility of the presence of metallic clusters.

None of the products analyzed showed any unusual line broadening in the Mössbauer spectra, other than a slight distribution in internal magnetic field. Therefore, a glassy or amorphous state in the products is precluded. Moreover, X-ray diffraction of each product did not show any crystallinity, and microcrystallinity (<200Å particle diameter) was ruled out by the absence of superparamagnetism, as shown by the above-discussed Mössbauer analyses. Therefore, the lack of crystallinity inferred from X-ray diffraction and IR spectroscopy may be due to interference from some magnetically inert organic matter.

The relatively small magnitude of both the isomer shift and the internal magnetic field of the iron product is consistent with formal $Fe^{+4}$ oxidation state with possible delocalization of charge on the aromatic ring, i.e., [Fe(ring)]$^{+4}$, and a fairly symmetrical environment. The latter can be attained by axial interaction with rings of neighboring molecules, which are believed to have become closer after partial pyrolysis. The isomer shift is a direct measure of the s-electron density at the nuclear probe, $^{57}$Fe, and is affected by the population of d-orbitals which can shield the s-electrons from the nucleus. The larger the s-electron density, the smaller the magnitude of isomer shift. The relatively small magnitude of isomer shift and internal magnetic fields for both the iron and cobalt products is believed to be caused by delocalization of electrons. This is supported by the fact that covalent compounds survived the electronic excitation during neutralization, following the Auger event, resulting in the loss of several electrons triggered by electron-capture decay of $^{57}$Co only when there is significant delocalization of electrons in the compound, e.g., when $^{57}$Co is bound to aromatic structures with $\pi$-electrons or when it is part of a metallic chain.

The elemental analysis of the product produced from the cobalt phthalocyanine compound indicates a cobalt-to-nitrogen ratio of about 1:4. Earlier investigations of thermal pyrolysis of metal phthalocyanines and porphins on a carbon substrate, conducted in an attempt to improve catalytic properties, also proposed the survival of the metal-$N_4$ moiety and the formation of a polyconjugated structure.

It is believed that, by the method of the present invention, the non-ferromagnetic porphin compound undergoes partial pyrolysis and retains an aromatic structure in the immediate vicinity of the central transition metal atom. It is believed that the distance between the coplanar rings of the structure is reduced and nitrogens or aromatic rings situated axially to the central transition metal atom are permitted to interact strongly, which leads to ferromagnetic interactions. The small magnitude of quadrupole splitting observed also supports a fairly symmetrical environment.

It Will be appreciate by those skilled in the art that changes could be made to the embodiments described above without departing from the broad inventive concept thereof. It is understood, therefore, that this invention is not limited to the particular embodiments disclosed, but it is intended to cover modifications within the spirit and scope of the invention as defined in the appended claims.

We claim:

1. A method for making a ferromagnetic porphin compound comprising heating a non-ferromagnetic porphin compound having a central transition metal atom in the non-ferromagnetic porphin molecule and having pyrrole rings of the non-ferromagnetic porphin molecule having benzene or phenyl groups substituted on or fused with said rings in the substantial absence atmospheric oxygen to a temperature sufficient to pyrolyze at least a portion of the benzene or phenyl groups of the non-ferromagnetic porphin compound, whereby a ferromagnetic porphin compound is formed.

2. The method according to claim 1, wherein the non-ferromagnetic porphin compound is selected from the group consisting of phthalocyanine and tetraphenylporphinate.

3. The method according to claim 1, wherein the non-ferromagnetic porphin compound is a $\beta$-crystalline phthalocyanine.

4. The method according to claim 1, wherein the transition metal is selected from the group consisting of cobalt, manganese, iron and nickel.

5. The method according to claim 1, wherein the non-ferromagnetic porphin compound is heated to a temperature of about 450° to about 700° C.

6. The method according to claim 5, wherein the temperature is about 600° C. to about 700° C.

7. The method according to claim 1, wherein the heating is carried out in the presence of an inert gas.

8. The method according to claim 7, wherein the inert gas is selected from the group consisting of argon and nitrogen.

9. The method according to claim 1, further comprising pretreating the non-ferromagnetic porphin compound to induce self-catalysis.

10. The method according to claim 9, wherein the temperature is less than about 475° C.

11. The method according to claim 9, wherein the non-ferromagnetic porphin compound is pretreated by exposure to gamma radiation.

12. The method according to claim 1, further comprising the step of exposing the ferromagnetic porphin compound to a magnetic field.

13. A ferromagnetic porphin compound produced according to the method of claim 1.

14. A ferromagnetic porphin compound produced according to the method of claim 9.

* * * * *